US010149653B1

(12) United States Patent
Tucker

(10) Patent No.: US 10,149,653 B1
(45) Date of Patent: *Dec. 11, 2018

(54) SECURE PATIENT DATA RECORDER FOR RECORDING MONITORED VITAL SIGN DATA

(71) Applicant: Guardian Dynamics, LLC, Charlotte, NC (US)

(72) Inventor: Peter L. Tucker, Fort Mill, SC (US)

(73) Assignee: Guardian Dynamics, LLC, Charlotte, NC (US)

( * ) Notice: Subject to any disclaimer, the term of this patent is extended or adjusted under 35 U.S.C. 154(b) by 668 days.

This patent is subject to a terminal disclaimer.

(21) Appl. No.: 14/724,651

(22) Filed: May 28, 2015

Related U.S. Application Data

(60) Continuation of application No. 12/268,111, filed on Nov. 10, 2008, now abandoned, which is a division of application No. 11/927,983, filed on Oct. 30, 2007, now abandoned, which is a division of application No. 10/249,655, filed on Apr. 29, 2003, now Pat. No. 7,338,443, application No. 14/724,651, which is a continuation of application No. 11/927,993, filed on Oct. 30, 2007, now Pat. No. 9,165,111, which is a continuation of application No. 10/249,655, filed on Apr. 29, 2003, now Pat. No. 7,338,443.

(60) Provisional application No. 60/376,262, filed on Apr. 29, 2002.

(51) Int. Cl.
*A61B 5/00* (2006.01)
*G06T 11/20* (2006.01)
*G06F 3/14* (2006.01)

(52) U.S. Cl.
CPC ............ *A61B 5/7445* (2013.01); *A61B 5/743* (2013.01); *G06F 3/14* (2013.01); *G06T 11/206* (2013.01); *A61B 2560/0271* (2013.01); *A61B 2560/045* (2013.01); *A61B 2560/0475* (2013.01)

(58) Field of Classification Search
CPC combination set(s) only.
See application file for complete search history.

(56) References Cited

U.S. PATENT DOCUMENTS

| | | |
|---|---|---|
| 4,216,462 A | 8/1980 | McGrath et al. |
| 5,181,519 A | 1/1993 | Bible |
| 5,331,549 A | 7/1994 | Crawford |

(Continued)

OTHER PUBLICATIONS

Information Disclosure Statement (IDS) Letter Regarding Common Patent Application(s), dated Oct. 6, 2015.

(Continued)

*Primary Examiner* — David C Eastwood
*Assistant Examiner* — Shirley Jian
(74) *Attorney, Agent, or Firm* — Tillman Wright, PLLC; James D. Wright; David R. Higgins

(57) ABSTRACT

A monitor and recorder system having a monitor unit for gathering vital sign data from a patient and a memory module for automatically recording the data. Means are provided for protecting the data from accidental or intentional deletion of the data or corruption or damage to the memory module without proper authorization. The data is recorded in a circular memory such that when data must be deleted, the last-recorded data is deleted first. A procedure is disclosed for preserving all data for at least a minimal period of time in case an event such as a patient death occurs.

23 Claims, 5 Drawing Sheets

(56) References Cited

U.S. PATENT DOCUMENTS

| | | |
|---|---|---|
| 5,375,604 A | 12/1994 | Kelly et al. |
| 5,502,989 A | 4/1996 | Murray et al. |
| 5,646,823 A | 7/1997 | Amori |
| 5,685,314 A | 11/1997 | Geheb et al. |
| 5,687,592 A | 11/1997 | Penniman et al. |
| 5,687,717 A | 11/1997 | Halpern et al. |
| 5,701,894 A | 12/1997 | Cherry et al. |
| 5,778,882 A | 4/1998 | Raymond et al. |
| 5,813,009 A | 9/1998 | Johnson et al. |
| 5,842,173 A | 11/1998 | Strum et al. |
| 5,842,468 A | 12/1998 | Denyer et al. |
| 5,842,978 A | 12/1998 | Levy |
| 5,845,240 A | 12/1998 | Fielder |
| 5,845,255 A | 12/1998 | Mayaud |
| 5,860,918 A | 1/1999 | Schradi et al. |
| 5,898,824 A | 4/1999 | Kato et al. |
| 5,907,291 A | 5/1999 | Chen et al. |
| 6,026,293 A | 2/2000 | Osborn |
| 6,083,156 A | 7/2000 | Lisiecki |
| 6,085,576 A | 7/2000 | Sunshine et al. |
| 6,093,146 A | 7/2000 | Filangeri |
| 6,095,985 A | 8/2000 | Raymond et al. |
| 6,183,417 B1 | 2/2001 | Geheb et al. |
| 6,205,419 B1 | 3/2001 | Fielder |
| 6,213,942 B1 | 4/2001 | Flach et al. |
| 6,219,230 B1 | 4/2001 | Cho |
| 6,221,010 B1 | 4/2001 | Maschke et al. |
| 6,249,717 B1 | 6/2001 | Nicholson et al. |
| 6,270,457 B1 | 8/2001 | Bardy |
| 6,305,197 B1 | 10/2001 | Ling |
| 6,364,834 B1 | 4/2002 | Reuss et al. |
| 6,490,513 B1 | 12/2002 | Fish et al. |
| 6,493,220 B1 | 12/2002 | Clark et al. |
| 6,537,268 B1 | 3/2003 | Gibson et al. |
| 6,542,910 B2 | 4/2003 | Cork et al. |
| 6,574,538 B2 * | 6/2003 | Sasaki .................. G07C 5/085 701/32.2 |
| 6,581,420 B1 | 6/2003 | Ling et al. |
| 6,671,808 B1 | 12/2003 | Abbott et al. |
| 6,790,178 B1 | 9/2004 | Mault et al. |
| 6,796,152 B1 | 9/2004 | Yu |
| 6,799,981 B1 | 10/2004 | Yu |
| 6,808,400 B2 | 10/2004 | Tu |
| 6,842,801 B2 | 1/2005 | Yamada |
| 6,886,061 B2 | 4/2005 | Yokota et al. |
| 7,275,941 B1 | 10/2007 | Bushby |
| 7,295,988 B1 | 11/2007 | Reeves |
| 7,338,443 B1 | 3/2008 | Tucker |
| 7,339,610 B2 * | 3/2008 | Kusaka .................. H04N 5/232 348/207.1 |
| 7,341,464 B2 | 3/2008 | Cuellar et al. |
| 7,549,161 B2 | 6/2009 | Poo et al. |
| 7,657,443 B2 | 2/2010 | Crass et al. |
| 7,698,154 B2 | 4/2010 | Marchosky |
| 7,722,369 B2 | 5/2010 | Bushby |
| 7,749,194 B2 | 7/2010 | Edwards et al. |
| 7,826,539 B2 | 11/2010 | Schneider et al. |
| 8,882,663 B1 | 11/2014 | Tucker |
| 2001/0020951 A1 * | 9/2001 | Onagawa .................. G06F 3/14 345/696 |
| 2002/0013518 A1 | 1/2002 | West et al. |
| 2002/0024512 A1 | 2/2002 | Terasawa et al. |
| 2002/0035422 A1 * | 3/2002 | Sasaki .................. G07C 5/085 701/32.2 |
| 2002/0053090 A1 | 5/2002 | Okayama et al. |
| 2002/0093575 A1 * | 7/2002 | Kusaka .................. H04N 5/232 348/231.9 |
| 2002/0120472 A1 | 8/2002 | Dvorak et al. |
| 2004/0027795 A1 | 2/2004 | Lee et al. |
| 2004/0074264 A1 | 4/2004 | Kung et al. |
| 2006/0064323 A1 | 3/2006 | Alleckson et al. |

OTHER PUBLICATIONS

"5.5 Error Checking" Kingston Technology Company, Inc. http://www.technick.net/public/code/cp_dpage.php?aiocp_dp=guide_umg_05_005, copyright 2000, accessed Apr. 23, 2010 (1 page).

* cited by examiner

SECURE PATIENT DATA RECORDER FOR RECORDING MONITORED VITAL SIGN DATA

CROSS REFERENCE TO RELATED APPLICATIONS

This application is:
(1) a continuation of, and claims priority under to, U.S. patent application Ser. No. 12/268,111, filed Nov. 10, 2008, which '111 application is a division of, and claims priority under 35 U.S.C. § 120 to, U.S. patent application Ser. No. 11/927,983, filed Oct. 30, 2007, now abandoned, which '983 application is a division of, and claims priority under 35 U.S.C. § 120 to, U.S. patent application Ser. No. 10/249,655, now U.S. Pat. No. 7,338,443, filed Apr. 29, 2003 and issued Mar. 4, 2008, and which '655 application is a nonprovisional of U.S. patent application Ser. No. 60/376,262, filed Apr. 29, 2002; and
(2) a continuation of, and claims priority under 35 U.S.C. § 120 to, U.S. patent application Ser. No. 11/927,993, filed Oct. 30, 2007, which application is a continuation of, and claims priority under 35 U.S.C. § 120 to, U.S. patent application Ser. No. 10/249,655, now U.S. Pat. No. 7,338,443, filed Apr. 29, 2003 and issued Mar. 4, 2008, and which '655 application is a nonprovisional of U.S. patent application Ser. No. 60/376,262, filed Apr. 29, 2002.

The entirety of each of the foregoing applications is incorporated herein by reference,

BACKGROUND OF THE PRESENT INVENTION

Field of the Present Invention

The present invention relates generally to the field of bedside patient vital sign monitors, and more particularly to methods and apparatuses for unavoidably recording vital sign data, gathered from a patient by a bedside monitor, in a secure memory device and protecting the data from deletion such that the data may be retrieved and examined by authorized personnel upon the death of the patient or upon the occurrence of another predetermined event.

Background

In recent years, the need for information concerning the circumstances surrounding patient injuries, deaths and other medical events has greatly increased. For example, medical research often depends on understanding the connection between the event and a particular biological characteristic, or on the correlation between two or more such characteristics. Ever-increasing medical malpractice litigation demands precise accountability in assessing liability. As a result, considerable effort is expended trying to reconstruct the circumstances around the medical event of interest.

One well-known source of biological information is the bedside monitor or other vital sign sensing device that is connected to many hospital, clinic or even home-care patients. Such devices are frequently used to monitor a patient's basic vital signs, such as respiration, temperature, heart rate and blood pressure; however, they may also be used to monitor a wide variety of other biological information instead of, or in addition to, the more common vital signs. Unfortunately, the information monitored is not typically preserved for later retrieval; if a record of the information is desired, it is typically printed out for preservation. If the monitored information is stored in a memory device at all, it is discarded before any subsequent investigation may take place. As a result, a very important potential source of information is lost.

Monitoring devices that preserve the data they monitor are well known in other environments. For example, flight data recorders, commonly known as "black boxes," are found on most large commercial airplanes, and similar recorders are present on many railroad locomotives. However, such black boxes are typically used solely for the purpose of recording data for subsequent retrieval, and are not actually used by the pilot or engineer while operating the airplane or locomotive. In addition, known black boxes are used to monitor operating conditions of a machine, rather than a human, and their operation is thus automatically interconnected to the operation of the machine itself. Moreover, airplanes and locomotives, unlike humans, have no general right to privacy, and thus do not face privacy concerns in the way that human monitoring systems must.

Thus, a need has existed for a patient monitoring system that operates automatically and securely preserves patient vital sign data for future investigation. In particular, a need exists for a "black box" recorder device that can operate in conjunction with a conventional bedside monitor unit such that the combined system may be easily implemented in hospitals and other healthcare facilities without the need for significant personnel training and that does not significantly raise the price of the monitor unit or the overall system.

All previously-known monitoring devices suffer from one or more drawbacks with regard to their use as a "black box," or secure patient data recorder. For example, although there are known to be monitoring devices that include means for recording gathered data, many merely record vital sign data temporarily, until it can be transmitted to a central collection point. Unfortunately, such an approach requires complicated communication procedures, fails to provide any protection for the memory device in the monitor unit, and makes the collected data available to a wide variety of users. For the investigative purposes commonly associated with a "black box" device, it is generally preferable to simplify the data storage mechanism, protect the integrity of the original memory device itself, and to minimize the accessibility of the device, and the data on the device, to a very small number of analysts. Thus, a need exists for a recorder device that is positioned in the same location as the monitor itself, but that can be readily protected.

Other monitoring and recording devices, such as those disclosed in U.S. Pat. No. 5,701,894 to Cherry et al. and U.S. Pat. No. 5,860,918 to Schradi et al., have means by which the stream of vital sign data gathered thereby is not continuously recorded. If a recorder device is not automatically operated whenever vital sign data is being gathered by the monitor, then its utility as a "black box" recorder may be easily subverted, and in any event these devices fail to disclose any protective mechanisms for the memory devices themselves.

A few known monitoring devices, such as those disclosed in U.S. Pat. Nos. 5,778,882 and 6,095,985 to Raymond et al. and U.S. Pat. No. 5,687,717 to Halpern et al., provide some software-based protection against unauthorized viewing of recorded vital sign data. Because it is frequently important to protect the confidentiality of patient data, such a function may be important. Unfortunately, the data protection offered by these systems does not protect the data stored on the modules from being overwritten or otherwise erased or corrupted. Thus, a need still exists for a recorder unit that prevents data deletion, and not just data access.

U.S. Pat. No. 6,270,457 to Bardy discloses a system and method of automated collection and analysis of monitored patient data. The data is collected from an implantable device from which the monitored data is periodically uploaded. Unfortunately, the only continuous recordation of which this system is capable is on the device that is implanted inside the patient's body, and such a device is inherently incapable of being used as a "black box" device.

Thus, a need still exists for a monitor and recorder system that may be placed adjacent a patient such that vital sign data gathered by the monitor device is always automatically recorded in a memory module and protected against accidental or intentional deletion, corruption or replacement except by authorized personnel.

SUMMARY OF THE PRESENT INVENTION

The system of the present invention is intended to provide assistance in reconstructing the circumstances surrounding a particular medical incident, such as the death of a patient by recording data gathered by bedside monitors on a patient data recorder. Like the "black boxes" used on airplanes, the primary advantage of this system is that the most relevant information describing a patient's current medical state is always automatically recorded for later retrieval if it becomes necessary. It is also believed that the presence of such a recorder would tend to encourage medical personnel to be more diligent and thorough in tending to their duties.

Because the circumstances under which such information becomes necessary are thus so serious (for example, a medical or even a legal investigation into the cause of a person's death), it is important to prevent the patient data recorder from being tampered with. Security is first provided by the limited means for inputting data into the device: the only data that may be input is vital sign information as described above. No means for erasing the data is provided, and the medium on which the data is stored is physically locked inside the unit.

The microprocessor or microprocessors in the system may be programmed to provide further security. For example, they may be programmed to prevent the patient data recorder from being "zeroed out" by operating the monitor with the sensing devices disconnected, or to enable operation only upon the entry of a valid code or password. The system may also have a separately input and protected clock to prevent a user from later changing the monitor's time and date and connecting the sensing devices to a healthy person to produce apparently normal readings. An encryption algorithm may also be included for encrypting the data stored in the patient data re such that only a peripheral device having corresponding software may be used to download the stored data.

Part or all of the patient data recorder may be easily removable for transport and storage. Further physical controls such as locks and other barriers may be utilized to prevent physical access to the device such that only a user with a proper key, tools, or know-how is capable of retrieving the device. The patient data recorder may also utilize a proprietary output connection to prevent users from connecting peripheral devices other than those intended to be connected.

In operation, the vital sign sensing devices are first connected or applied to a patient. Information identifying the patient is entered input into the monitor unit, and the sensing devices begin collecting vital sign data from the patient. The vital sign data gathered from the patient is relayed to the monitor unit, where it may be displayed on one or more of the display devices. At the same time, the vital sign data, together with the patient identification information and date/time stamp information, is relayed to the patient data recorder and stored therein. No other means is provided for entering data into the patient data recorder, so the only data residing in the patient data recorder, other than any portion of the software application, is patient data. The data is stored in such a form and amount that vital sign data covering an extended period of time, such as a day, a week or even a month, may be stored simultaneously therein. When the available memory in the memory module is exhausted, further data may be stored in those locations in the memory module which currently hold the oldest data, so that data corresponding to the most recent time period is always present. Alternatively, the memory module may be replaced on a periodic basis, with the frequency chosen such that the available memory space in the memory module is never completely exhausted.

When a need arises to investigate a particular medical phenomenon, such as the death of a patient or a particular medical condition occurring in a patient, the memory module may be removed from the patient data recorder and subsequently installed in a suitable peripheral device, such as a personal computer, and the data examined.

The present invention comprises a secure data recorder communicatively connected to a monitor unit to automatically record patient vital sign data on a memory module and to protect the memory module and the data from damage. Broadly defined, the present invention, according to one aspect, is a method of recording patient vital sign data and includes the steps of providing a monitor and recorder system, the monitor and recorder system including a monitor unit, having at least one sensing device, and a memory module; facilitating the arrangement of the at least one sensing device in operative relationship with a patient; during operation of the monitor and recorder system, automatically determining whether the memory module is prepared to accept vital sign information gathered by the monitor unit; if the memory module is prepared to accept vital sign information, gathering vital sign information from the patient via the monitor unit and recording data representative of at least some of the vital sign information on the memory module; and if the memory module is not prepared to accept vital sign information, preventing the monitor unit from gathering vital sign information.

In features of this aspect, the monitor and recorder system is a bedside monitor and recorder device, the method further includes the step of positioning the monitor and recorder system adjacent the patient, and if the memory module is prepared to accept vital sign information, then the method further includes the step of displaying, on the monitor unit, a graphical representation of the vital sign information as it is gathered from the patient; the step of automatically determining whether the memory module is prepared to accept vital sign information includes automatically determining whether the memory module is properly installed in the monitor recorder device; the step of automatically determining whether the memory module is prepared to accept vital sign information includes determining whether memory space in the memory module is available to receive vital sign data; the step of determining whether memory space is available includes determining whether a predetermined amount of memory space is available; the step of automatically determining whether the memory module is prepared to accept vital sign information includes determining whether input, representative of authorization from a user to record new data in the memory module, has been received by the bedside monitor and recorder device; if it is determined that the memory module is not prepared to accept vital sign information, then the method further includes providing an indication, to a user, that the monitor and recorder system is inoperable; if it is determined that the memory module is not prepared to accept vital sign information, then the method further includes receiving input, from the user, instructing the monitor unit to gather vital sign data, and gathering vital sign information from the patient via the monitor unit without recording data representative of the vital sign information on the memory module; the step of providing a monitor and recorder system includes providing a modular monitor unit having a plurality of module interfaces for connecting monitor modules to the monitor unit; and the step of providing a monitor and recorder system includes providing at least one monitor module, having a sensing device connected thereto, for connection to the monitor unit via one of the plurality of module interfaces.

In another aspect of the present invention, a monitor and recorder device includes a monitor unit that gathers data representative of vital sign information from patients via at least one sensing device; a secure patient data recorder, disposed adjacent to the monitor unit, having a memory module; a controller, interposed between the at least one sensing device and the memory module, that relays data gathered by the monitor unit to the memory module for recordation therein; and an interlock system that prevents the monitor unit from gathering the data without also recording the data in the memory module.

In features of this aspect, the monitor and recorder device is a bedside monitor and recorder device, and the monitor unit includes an electronic display device that displays a graphical representation of the vital sign information as it is gathered from the patient; the memory module includes a physical output that produces a signal indicative of whether the memory module is enabled to record gathered data, and the interlock system includes a circuit that determines the status of the signal produced at the physical output of the memory module; the interlock system includes software that analyzes whether the memory module is enabled to record gathered data; the monitor unit is a modular monitor unit having a plurality of module interfaces for connecting monitor modules to the monitor unit; and the monitor unit includes at least one monitor module, having a sensing device connected thereto, connected to the monitor unit via one of the plurality of module interfaces.

In yet another aspect of the present invention, a method of monitoring patient vital sign data includes providing a monitor unit having at least one sensing device; facilitating the arrangement of the at least one sensing device in operative relationship with a patient; during operation of the monitor unit, automatically determining whether an operable patient data recorder is communicatively connected to the monitor unit; if an operable patient data recorder is communicatively connected to the monitor unit, gathering vital sign data from the patient via the monitor unit and transmitting data representative of at least some of the vital sign data to the patient data recorder for recordation therein; and, if an operable patient data recorder is not communicatively connected to the monitor unit, preventing the monitor unit from gathering vital sign data.

In features of this aspect, the step of automatically determining whether an operable patient data recorder is communicatively connected to the monitor unit includes automatically determining whether a patient data recorder has a memory module that is prepared to accept vital sign data gathered by the monitor unit; the monitor unit is a bedside monitor unit, and if the memory module is prepared to accept vital sign data, then the method further comprises the step of displaying, on the monitor unit, a graphical representation of the vital sign information as it is gathered from the patient; the step of automatically determining whether the memory module is prepared to accept vital sign information includes automatically determining whether the memory module is properly installed in the monitor recorder device; the step of automatically determining whether the memory module is prepared to accept vital sign information includes determining whether memory space in the memory module is available to receive vital sign data; the step of determining whether memory space is available includes determining whether a predetermined amount of memory space is available; and the step of automatically determining whether the memory module is prepared to accept vital sign information includes determining whether input, representative of authorization from a user to record new data in the memory module, has been received by the bedside monitor and recorder device.

In additional features of this aspect, if it is determined that the memory module is not prepared to accept vital sign information, then the method further comprises the step of providing an indication, to a user, that the monitor and recorder system is inoperable; if it is determined that the memory module is not prepared to accept vital sign information, then the method further includes receiving input, from the user, instructing the monitor unit to gather vital sign data, and gathering vital sign information from the patient via the monitor unit without recording data representative of the vital sign information on the memory module; the step of automatically determining whether an operable patient data recorder is communicatively connected to the monitor unit includes attempting to establish wireless communication between the monitor unit and an operable patient data recorder; the step of automatically determining whether an operable patient data recorder is communicatively connected to the monitor unit includes attempting to establish non-wireless communication between the monitor unit and an operable patient data recorder; the step of providing a monitor unit includes providing a modular monitor unit having a plurality of module interfaces for connecting monitor modules to the monitor unit; and the step of providing a monitor unit includes providing at least one monitor module, having a sensing device connected thereto, for connection to the monitor unit via one of the plurality of module interfaces.

In still another aspect of the present invention, a monitor and recorder system includes a monitor unit that gathers vital sign information from patients; and a secure patient data recorder that records data representing at least some of the vital sign information, wherein the patient data recorder includes a memory module, an enclosure substantially surrounding the memory module and having a removable structural portion for providing user access to the memory module, and a lock that maintains the removable structural portion in a locked position, thereby preventing the memory module from being removed.

In features of this aspect, the removable structural portion is an access portal; the removable structural portion encompasses substantially all of the enclosure; the patient data recorder is structurally connected to the monitor unit; the monitor unit and the patient data recorder share the enclosure; the monitor and recorder system is a bedside monitor and recorder device, and the monitor unit includes an electronic display device that displays a graphical representation of the vital sign information as it is gathered from the patient; the monitor unit is a modular monitor unit having a plurality of module interfaces for connecting monitor modules to the monitor unit; and the monitor unit includes at least one monitor module, having a sensing device connected thereto, connected to the monitor unit via one of the plurality of module interfaces.

In still another aspect of the present invention, a method of securely recording patient data includes the steps of defining, in a memory module, an addressable memory space for recording data representing vital sign information from a patient; operating a monitor unit for a period of time, the period of time defining a monitoring period; during the monitoring period, continuously and repeatedly gathering, via the monitor unit, data representative of vital sign information from a patient; recording the data in the memory space, as it is gathered, by way of determining the location, in the addressable memory space, that contains the oldest previously-recorded data, and recording the newly-gathered data in the determined location; discontinuing the gathering step at the end of the monitoring period; and semi-permanently retaining, in the memory module, substantially all of the vital sign data that is stored in the memory module at the time the gathering step is discontinued.

In features of this aspect, the method further includes the step of providing a bedside monitor unit having an electronic display device that displays a graphical representation of the vital sign data as it is gathered from the patient, where the bedside monitor unit is the monitor unit utilized in the gathering step; the memory module is a non-volatile memory device; the step of determining the location of the oldest previously-recorded data includes tracking the age of all data stored in the memory space; the step of tracking the age of all data stored in the memory space includes recording an indication of the sequence in which data was stored; the step of tracking the age of all data stored in the memory space includes recording an indication of the time that the data was stored; the step of recording the newly-gathered data in the determined location is carried out only when the addressable memory space becomes substantially filled; the step of semi-permanently retaining substantially all of the vital sign data includes preventing unauthorized deletion, from the memory module, of any of the vital sign data that is stored in the memory module at the time the gathering step is discontinued until an input, representative of an authorization to delete, is received by the memory module; the method further includes erasing substantially all of the defined memory space upon receiving the authorization input; upon receiving the authorization input, the method further includes permitting the data retained in the defined memory space to be overwritten based on the location-determining step; the step of providing a bedside monitor unit includes providing a modular monitor unit having a plurality of module interfaces for connecting monitor modules to the bedside monitor unit; and the step of providing a bedside monitor unit includes providing at least one monitor module, having a sensing device connected thereto, for connection to the bedside monitor unit via one of the plurality of module interfaces.

In still another aspect of the present invention, a method of securely recording patient data includes the steps of providing a monitor and recorder system having a monitor unit, with at least one sensing device, and a memory module; facilitating the arrangement of the at least one sensing device in operative relationship with a patient; continuously and repeatedly gathering, via the monitor unit, data representative of vital sign information from the patient; as the vital sign data is gathered, recording the data on the memory module; and preventing unauthorized access to the vital sign data recorded on the memory module.

In features of this aspect, the monitor and recorder system is a bedside monitor and recorder device, and the method further includes displaying, on the monitor unit, a graphical representation of the vital sign information as it is gathered from the patient; the step of preventing unauthorized access to the vital sign data recorded on the memory module includes preventing the unauthorized deletion of the recorded vital sign data from the memory module, the method further comprises the step of receiving, from a user, input representative of authorization to delete data, and the step of preventing the unauthorized deletion of data includes deleting data only upon the receipt of the authorization; the vital sign data that is present in the memory module at the time the gathering step is discontinued defines protected data, and the step of preventing includes preserving substantially all of the protected data until the monitor and recorder device receives the input representative of authorization to delete data; the step of preventing unauthorized data deletion includes locking the memory module in an enclosure, and providing physical access to the memory module only when the memory module is unlocked; the step of preventing data deletion includes soliciting, from a user, input representative of a password, receiving input from the user, and permitting data to be deleted from the memory module only when the input supplied by the user matches a pre-established password; and the received input is first input, and the method further includes soliciting, from the user, input identifying the user, receiving second input from the user, and permitting data to be deleted from the memory module only when the second input corresponds to a user having authority to delete data from the memory module.

In additional features of this aspect, the method further includes preserving, in the memory module, substantially all of the vital sign data that is stored in the memory module at the time the gathering step is discontinued, and the step of preventing the unauthorized deletion of data includes preventing the unauthorized deletion of the preserved data; the patient is a first patient, and the method further includes positioning the bedside monitor and recorder device adjacent a second patient after the gathering step is discontinued, continuously and repeatedly gathering, via the monitor unit, data representative of vital sign information from the second patient, and as the vital sign data is gathered, recording the data on the memory module, wherein the step of preventing the unauthorized deletion of the recorded data representing vital sign information from the first patient includes preventing the unauthorized deletion of the data representing vital sign information from the first patient while recording the data representing vital sign information from the second patient; the step of preventing unauthorized access to the vital sign data recorded on the memory module includes preventing the recorded vital sign data from being viewed without authorization; the step of preventing unauthorized access to the vital sign data recorded on the memory module includes preventing the recorded vital sign data from being downloaded without authorization; the step of providing a monitor and recorder system includes providing a modular monitor unit having a plurality of module interfaces for connecting monitor modules to the monitor unit; and the step of providing a monitor and recorder system includes providing at least one monitor module, having a sensing device connected thereto, for connection to the monitor unit via one of the plurality of module interfaces.

In still another aspect of the present invention, a method of recording patient vital sign data includes providing a monitor and recorder system having a monitor unit, with at least one sensing device, and a memory module; facilitating the arrangement of the at least one sensing device in operative relationship with a patient; at the monitor unit, gathering data via the at least one vital sign sensing device; analyzing the data to assess whether the gathered data represents valid vital sign information; if the data is determined to be valid vital sign information, recording at least some of the data on the memory module; and if the data is determined not to be valid vital sign information, preventing the monitor unit from recording the data.

In features of this aspect, the step of analyzing the data includes determining whether the data varies over a predetermined period of time; the data includes data values, and the step of analyzing the data includes determining whether the data values fall outside a predetermined range; the step of determining includes determining whether any data value falls outside the predetermined range; the step of determining includes determining whether a predetermined number of successive data values fall outside the predetermined range; the step of providing a monitor and recorder system includes providing a modular monitor unit having a plurality of module interfaces for connecting monitor modules to the monitor unit; the step of providing a monitor and recorder system includes providing at least one monitor module, having a sensing device connected thereto, for connection to the monitor unit via one of the plurality of module interfaces; the method further includes positioning the memory module in a different room from where the monitor unit is positioned; and the method further includes wirelessly communicating the gathered data from the monitor unit to the memory module.

In still another aspect of the present invention, a method of preserving patient vital sign data in a health care facility includes the procedure of, when gathering vital sign information from a patient, automatically recording data, representative of the gathered information, on a memory module; preserving the data for a predetermined period of time; upon the occurrence of an event of a predetermined type during the predetermined period of time, retrieving the recorded data from the memory module for examination; and if an event of a predetermined type does not occur within the predetermined period of time, authorizing the deletion of the data from the memory module.

In features of this aspect, the gathering step includes gathering vital sign information from a patient via a monitor unit, and the memory module is disposed adjacent to, and communicatively connected with, the monitor unit; the monitor unit is a bedside monitor unit, and the method further includes displaying, on the monitor unit, a graphical representation of the vital sign information as it is gathered from the patient; the procedure is carried out for each of at least a majority of the patients treated at the health care facility; the determination of whether an event of a predetermined type occurs during the predetermined period of time is made manually; the method further includes designating at least one user to authorize the deletion of the data from the memory module; at least one predetermined event type is the death of the patient; the method further includes positioning the memory module in a different room from where the monitor unit is positioned; the method further includes wirelessly communicating the gathered data from the monitor unit to the memory module; if the deletion of the data is authorized, then the procedure further includes deleting the data from the memory module; the deleting step is carried out immediately upon being authorized; and the deleting step is not carried out until it is necessary to record new vital sign data on the memory module.

BRIEF DESCRIPTION OF THE DRAWINGS

Further features, embodiments, and advantages of the present invention will become apparent from the following detailed description with reference to the drawings, wherein.

DETAILED DESCRIPTION OF THE PREFERRED EMBODIMENTS

Figure 1A:
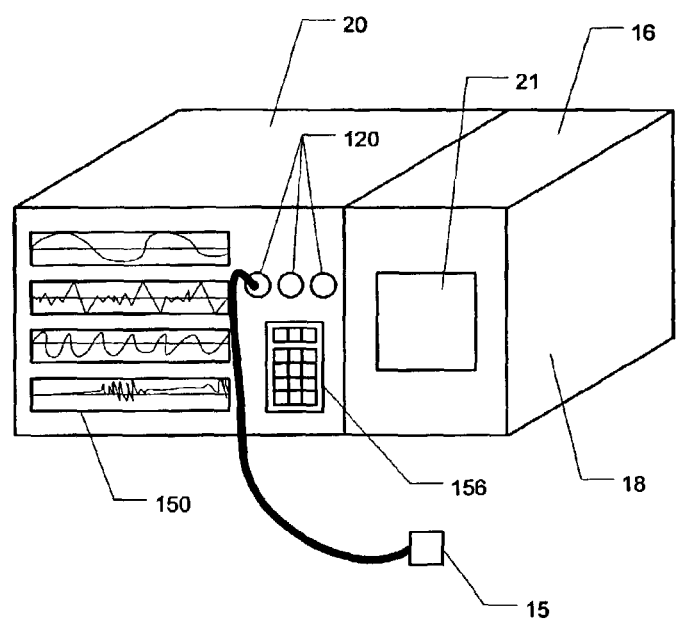
FIG. 1A is a perspective view of a monitor/recorder system in accordance with a first preferred embodiment of the present invention.

FIG. 1A is a perspective view of a monitor/recorder system 10 in accordance with a first preferred embodiment of the present invention. The monitor/recorder system 10 comprises a monitor unit 20, at least one sensing device 15 and a patient data recorder 16. A wide variety of sensing devices 15 are known for monitoring various patient data, many of which are commonly referred to as the patient's "vital signs." Data which may be monitored include, but are not limited to, such commonly-monitored data as oxygen saturation; heart rate; respiration rate; systolic, diastolic and mean arterial and pulmonary arterial blood pressures; electrocardiogram ("ECG" or "EKG") levels; and temperature; as well as such less commonly-monitored data as inspired minimum and end-tidal $CO_2$ levels; end-tidal volume and pressure; fractional inspired $O_2$; cardiac output; electroencephalogram ("EEG") levels; pulmonary wedge pressure; intercranial pressure; bispectral index monitoring ("BIS") levels of brain wave activity; and the settings for various respirators, including anesthesia respirators, ICU respirators and long-term respirators. Preferably, for reasons that will become apparent hereinbelow, four particularly important vital signs are usually monitored: respiration, temperature, heart rate, and blood pressure. However, it should be apparent that any combination of vital signs may be monitored without departing from the scope of the present invention. Appropriate sensing devices for each type of measurement exist in the form of probes, leads, and the like, and their design and selection are well known to those of ordinary skill in the art. The sensing devices 15 are each communicatively connected to sensor inputs 120 on the monitor unit 20.

Figure 1B:
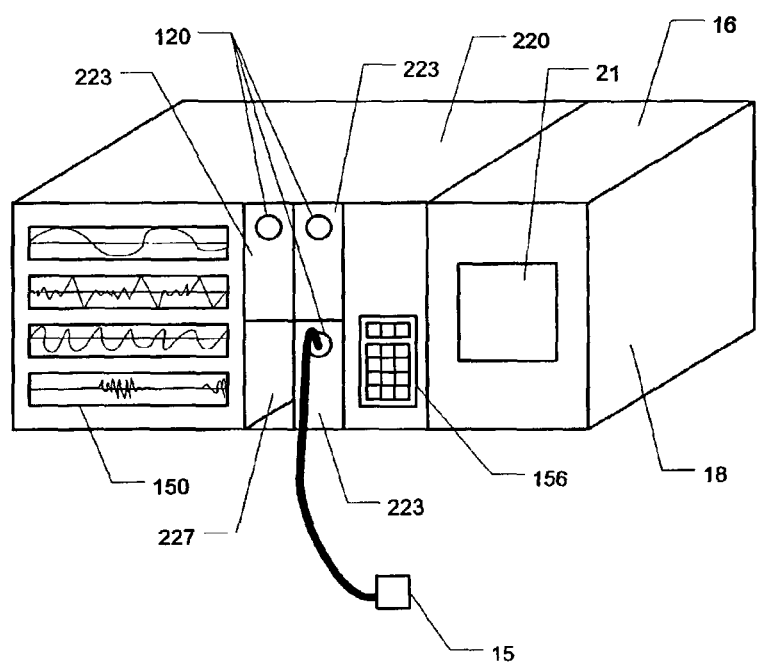
FIG. 1B is a perspective view of a monitor/recorder system in accordance with a second preferred embodiment of the present invention.

FIG. 1B is a perspective view of a monitor/recorder system 210 in accordance with a second preferred embodiment of the present invention. Like the monitor/recorder system 10 illustrated in FIG. 1A, this monitor/recorder system 210 comprises a monitor unit 220, at least one sensing device 15 and a patient data recorder 16. However, unlike the monitor/recorder system 210 of the first embodiment, the monitor unit 220 is a modular monitor that includes a plurality of module slots 227, each including a module interface (not shown) into which any of a variety of individual monitor modules 223 may be inserted. Generally, each monitor module 223 includes at least one sensor input 120 adapted to interconnect with a sensing device 15 appropriate for sensing or monitoring a particular type of vital sign data. Thus, a variety of monitor modules 223 are utilized with each modular monitor unit 220 in order to facilitate the simultaneous monitoring of a plurality of vital signs.

Regardless of the type of monitor unit 20, 220 that is utilized, the design and operation of a monitor unit 20, 220 that would be suitable for use with the present invention would be readily understood by one of ordinary skill in the art. However, a brief overview is presented here to highlight some of the important features of the present invention. Although the following discussion generally contemplates the use of a monitor unit 20 of the type illustrated in FIG. 1A, it should be apparent that the features of the present invention are applicable with a wide variety of monitor types, including types not illustrated herein.

Figure 2:
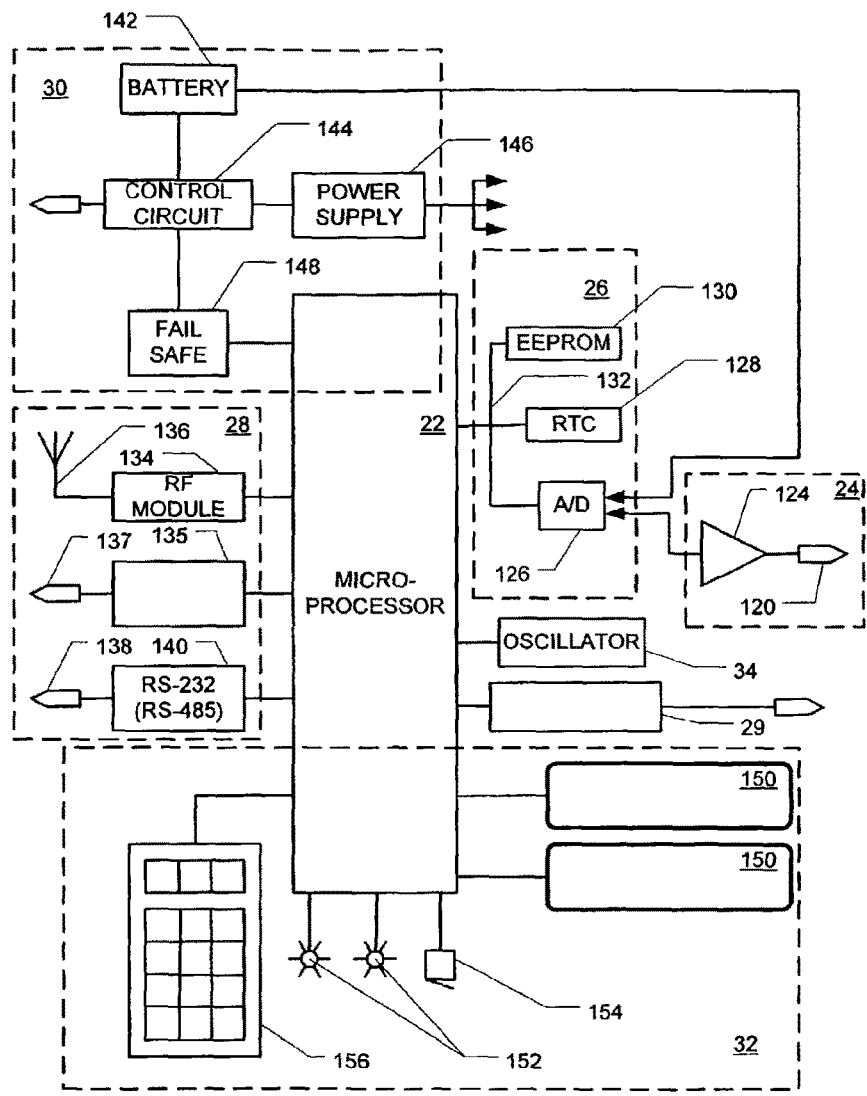
FIG. 2 is a block diagram of the hardware components of the monitor unit of FIG. 1A in accordance with a preferred embodiment of the present invention.

The monitor unit 20 illustrated in FIG. 1A includes both hardware and software components. FIG. 2 is a block diagram of the hardware components of the monitor unit 20 of FIG. 1A in accordance with the preferred embodiments of the present invention. The monitor unit hardware includes a microprocessor 22 and a variety of peripheral components and may be surface mounted on a single printed circuit board. The microprocessor 22 is preferably a 9-bit processor with at least 8 K of program memory. A microprocessor suitable for use with the present invention is the Motorola MC68HC705. The peripheral components include a patient data input subsystem 24 for providing patient data, an onboard data subsystem 26 for providing data developed or stored within the monitor unit 20 to the microprocessor 22, a data recorder interface 29 for communicating with the patient data recorder 16, a power subsystem 30, a user interface subsystem 32 and an oscillator 34. The patient data input subsystem 24 includes at least one sensor input 120 and an amplification stage 124. Each sensor input 120 is equipped to physically connect with a patient data sensing device 15. Each input 120 may be specifically designed for a particular type of sensing device 15 or may be of a generic design to enable connection with different types of sensing devices 15. Each sensing device 15 typically generates a small analog signal based on the particular data being measured, monitored, sensed or the like. The respective signals generated at each sensor input 120 are amplified by the amplification stage 124 and provided as inputs to the onboard data subsystem 26.

The onboard data subsystem 26 includes at least one analog-to-digital ("A/D") converter 126, a real-time clock ("RTC") 128, and an EEPROM 130, each of which is connected to the microprocessor 22 via a serial peripheral interface ("SPI") bus 132. The A/D converter 126, which may be a 12-bit bipolar input A/D converter of a well-known type, periodically accepts input signals from the patient data input subsystem 24 and from the battery pack 142 and converts each respective voltage level to a digital value. The RTC 128 keeps track of real-time time and day information and provides this information to the microprocessor 22 upon request at power-on. It has its own crystal oscillator and power backup circuitry. The EEPROM 130 is used to store parameters when the monitor unit 20 is powered off.

The power subsystem 30 preferably includes a battery pack 142, a battery control circuit 144, a power supply 146 and a battery fail safe 148. The battery pack 142 may be provided to permit the monitor unit 20 to operate without an external AC (wall) power source for an extended period of time, which may be several days or more, in order to provide functionality in locations where an external power source is not available, or it may be provided merely to provide backup power in the event of a temporary power failure at the hospital or other facility at which the system 10 is used. Alternatively, the battery pack 142 and battery control circuit 144 may be omitted entirely if the monitor unit 20 is to operate exclusively on power from an external power source. If the monitor unit 20 is to be operable using power from a battery pack 142, then the battery control circuit 144 may further include other elements not shown in the drawings. For example, the battery control circuit 144 may include a power source recognition circuit, which determines whether the monitor unit 20 is currently connected to an external power source, and a battery charging circuit, which utilizes the external power source to recharge the battery pack 142.

In a preferred embodiment, the battery pack 142 includes NiCad batteries that are designed for complete charging within several hours. Such a battery pack 142 preferably operates in at least two modes: rapid charging and trickle charging. When recharging a depleted battery pack 142, rapid charging may first be employed to quickly recharge the battery pack 142 at 1 C (500 mA) to its fully charged level. After a predetermined period, or when the power supplied by the battery pack 142 settles on a constant voltage level or begins to drop, the battery control circuit 144 may switch from rapid charging to trickle charging, whereby the voltage level is maintained with a trickle charge at 0.1 C (75 mA) for as long as the battery control circuit 144 remains connected to the external power source. The power supply 146 includes a simple DC-DC switcher circuit to convert the output of the battery pack 142 to a suitable level (for example, +5 volts), and an additional converter to generate a corresponding negative voltage (for example, −5 volts) for the monitor unit's analog circuits. The battery fail safe 148 monitors the battery pack voltage levels and triggers a controlled shutdown of the microprocessor 22 in the event the battery pack 142 becomes excessively depleted during operation, thus preventing loss of data or damage to the monitor unit 20.

The user interface subsystem 32 preferably includes at least one display unit 150 and a keypad 156 and may further include one or more indicator lights 152, one or more audio alarms 154, and other suitable user interface devices. Each display unit 150 may include means for displaying data, representing the human parameters being monitored, to a user in a known graphical, numerical and/or textual format. Preferably, the user interface subsystem 32 includes a plurality of display units 150, one or more of the display units 150 include a plurality of display areas, or both. In a preferred embodiment, the display units 150 includes an LED-type display that includes separate graphical displays for the historical display of different monitored parameters and numerical displays for current values of the parameters. The display units 150 may also include one or more separate microcontrollers or other graphics processors to more efficiently process and display the data being gathered. Each display unit 150 communicates with the microprocessor 22 via an interface that includes a data bus of sufficient bitwidth to handle the volume of data being displayed and a factory-preset contrast adjustment resistor. If included, the indicator lights 152 and the audio alarm 154 may be controlled by the microprocessor 22 to provide a user with visual or aural indications, respectively, of certain predefined conditions. The keypad 156 may be a standard membrane keypad wired in a simple X-Y matrix. Other switches, buttons, controls, dials, and the like may likewise be included as they would in typical commercially-available monitor units.

In addition to the components described hereinabove, the hardware components of the monitor unit 20 may also include a communications subsystem 28 for the external communication of data collected by the sensing devices 15. If included, the communications subsystem 28 preferably includes means for communicating with both a communications network as well as a connection for communicating directly with another device, such as a personal computer. The connection to the communications network enables patient data to be monitored remotely; i.e., to be monitored by users or devices that are not physically present in the room in which the monitor unit 20 is located. The connection with the communications network may be made via either a wired connection or wirelessly. The type of interface used to facilitate the wired connection is dependent upon the communications network selected, but because the most standard communications network in commercial use today is an Ethernet-type network, the interface is preferably a 10/100 Base-T Fast Ethernet controller 135 using an RJ-45 connector 137.

If wireless communication is to be enabled, the communications subsystem 28 may include a RF modem 134 and an antenna 136. The RF modem 134 is preferably of minimal size and of a type capable of communicating using one or more market standard wireless communication protocols. More preferably, the RF modem 134 is a 900 MHz serial communications unit. RF modems suitable for use with the present invention include the 9XStream™ series of wireless modems available from MaxStream, Inc. of Orem, Utah. The antenna 136 may be an external antenna with a size concomitant with the overall size of the monitor unit 20. In a preferred embodiment, the antenna 136 is about 4 inches long and mounted on the monitor unit's enclosure.

The connection for communicating directly with another device, such as a personal computer, may include a serial I/O port 138 and one or more serial interfaces 140. Together, these components make it possible to connect other devices directly to the microprocessor 22. In a preferred embodiment, the serial I/O port 138 has a fixed baud rate of 9600 N-8-1, standard ASCII. Preferably, at least one standard interface, such as an RS-232 or RS-485 interface, or both, is provided to facilitate such communications. Devices, such as a personal computer, other peripheral components, and the like, that have a similar interface may then communicate directly with the monitor unit 20.

The data recorder interface 29 facilitates communication between the microprocessor 22 and the patient data recorder 16. A variety of such interfaces are well known to those of ordinary skill in the art. In an embodiment suitable for use with the present invention, the interface 29 is a standard PCMCIA interface with a suitable physical connection to the patient data recorder 16.

The operation of the microprocessor 22 and the peripheral components is controlled by the software components of the monitor unit 20. The software is preferably in the form of microcode, which may be stored in the program memory of the microprocessor 22. The microcode preferably includes multiple modules, each of which supports a particular function or device, linked together by a support program. This permits the modules to be written independently and later linked together to form the final code. The modules, which are preferably written in assembly language, may include a number of modules for performing more or less basic functions, including the following: Initialize, Main, User Interface, Keypad, Display, Clock, Sensing Devices, SD_Convert, SD_Tables, Battery Status, Battery Charger, User Serial Port, Network Serial In, Network Serial Out, A/D Converter, Math, Timer_IRQ, Checksum, Maintenance, Internal Self-Test, and Store Data. Notably, if more than one sensing device 15 is utilized, additional SD_Tables and SD_Convert modules may be necessary. The modules may also include some modules which are more specialized, such as graphics-oriented modules or modules for controlling the operation of specialized sensing devices 15. The actual code for each module may be easily developed by one of ordinary skill in the art.

The function of each of these modules is briefly described in Table 1.

TABLE 1

| Module | Function |
| --- | --- |
| Initialize | Initializes the microprocessor and peripheral components such as the display and sets up the software startup variables |
| Main | Controls general operation of module by processing "events" as they are received |
| User Interface | Receives keypad entries via the Keypad module and responds based on user interface algorithm |
| Keypad | Scans the keypad to detect a key press and returns the key location to the User Interface module |
| Display | Sends message packets from the User Interface module to a display unit for display |
| Clock | Interfaces with RTC to gather time and day information |
| Sensing Devices | Determines what sensing devices are installed in the unit |
| SD_Convert | Uses subroutines to return the current value measured or returned by a selected sensing device |
| SD_Tables | Converts a relative number from A/D Converter, representing a patient vital sign measurement, to an actual patient vital sign value using a lookup table corresponding to the sensing device type (the table being appropriately-sized to cover a desired range of possible values for the particular vital sign being monitored) |
| Battery Status | Monitors the voltage level of the battery and 1) provides the user with one or more "low battery" indications, and 2) halts the operation of the monitor unit when the battery is "dead" |
| Battery Charger | Determines whether battery charger is installed and controls the battery charging sequence |
| Serial Port | Sends/receives data to/from the serial I/O port |
| Host Serial In | Receives packets of data from the communications network via the appropriate network connection |
| Host Serial Out | Transmits packets of data to the communications network via the appropriate network connection |
| A/D Converter | Converts the thermocouple output voltage levels and battery voltage level to relative numbers |
| Math | Performs simple math operations required by SD_Convert and SD_Tables to support interpolation of measured values |
| Timer_IRQ | Triggers initiation of other operations and provides timeout timers for error testing |
| Checksum | Tests the program memory by calculating a checksum of the program memory and comparing the result to a previously-calculated value |
| Maintenance | Receives command packets via the serial I/O port and returns requested test information |
| Internal Self-Test | Verifies operability of program memory, EEPROM, A/D converter, and the like |
| Store Data | Packages data samples and control information into standard data blocks for storage in the patient data recorder |

Figure 3:
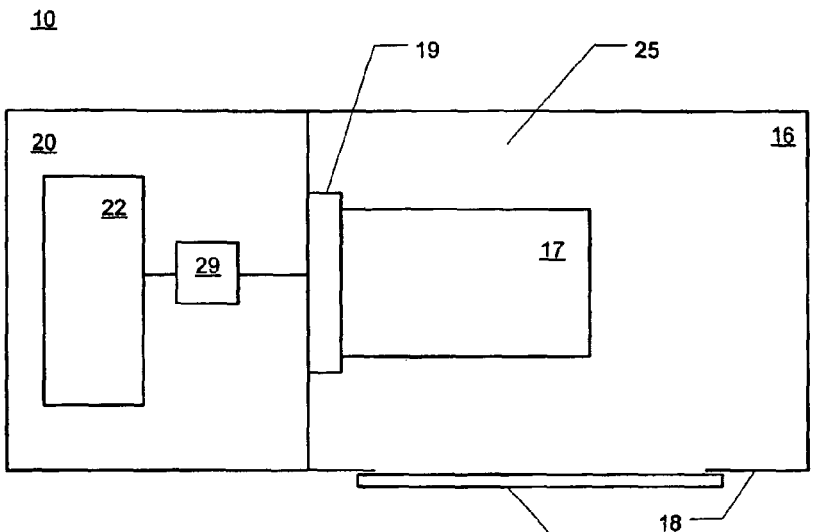
FIG. 3 is a schematic diagram of the monitor/recorder system of FIG. 1A illustrating the components of the patient data recorder in accordance with a preferred embodiment of the present invention.

FIG. 3 is a schematic diagram of the monitor/recorder system 10 of FIG. 1A illustrating the components of the patient data recorder 16 in accordance with a preferred embodiment of the present invention. The patient data recorder 16 includes an enclosure 18, a memory module 17, and a connector 19. The enclosure 18 is preferably a substantially closed structure of rugged construction for securely retaining the memory module 17 inside. The enclosure 18 may be an integral or built-in portion of the monitor unit 20, a separate structure securely fastened to the exterior of the monitor unit 20, or the like. In one embodiment, the enclosure 18 and monitor unit 20 are arranged as a single unitary object in order to provide added security, ease of installation, and evidence of tampering. However, in an alternative embodiment, the enclosure 18 may be locked or otherwise secured to the monitor unit 20 according to the principles described hereinbelow. In another alternative embodiment not illustrated herein, the enclosure 18 may be only a partial enclosure that is designed merely to block conventional removal of the memory module 17 therefrom. Other arrangements may also be possible without departing from the scope of the present invention.

The enclosure 18 includes an interior compartment 25 in which the memory module 17 is mounted and an access portal 21 through which the memory module 17 may be accessed. Preferably, the access portal 21 includes a door or similar structure that may be easily opened and closed when not secured. However, the exact structure of the access portal 21 may depend upon the form of the rest of the enclosure 18. For example, if the enclosure 18 is of a type designed only to prevent the conventional removal of the memory module 17, then the access portal 21 may be a metal bar secured in such a way as to prevent the memory module 17 from being pulled from its connector 19. Other types of access portal 21 will be apparent to persons skilled in the art.

Although not shown, the access portal 21 preferably includes one or more security devices to prevent unauthorized entry into the interior compartment 25. Security devices suitable for use with the present invention range from the simplistic to the sophisticated, with each type providing a level of security that corresponds generally to the sophistication level. For example, the access portal 21 may be secured using only one or more fastener, such as a set of screws with standard-type heads. Although such fasteners could be easily removed with a standard tool, the fasteners would at least prevent accidental entry by a patient or by a facility staff member. Further security could be provided by using fasteners with non-standard heads, thus requiring the use of a special tool to gain access to the interior compartment 25. For increased security, however, the access portal 21 may be provided with one or more locks or locking mechanisms. A wide variety of locks and related mechanisms are known, but locks suitable for use with the present invention may include hasp locks, padlocks, cylinder locks, socket-key locks, electronic locks, and the like, and may be combination locks or key locks. Depending on the type and size of lock chosen, appropriate lugs, rings, and the like may be disposed on the access portal 21 or the remainder of the enclosure 18 in order to accommodate the locks themselves.

The connector 19 is preferably disposed on or near one of the outer walls of the enclosure 18 to facilitate easy connection to the data recorder interface 29 in the monitor unit 20 and to provide a mounting location and electrical connection for the memory module 17. The connector 19 faces inwardly toward the interior compartment 25 of the enclosure 18 to facilitate installation and removal of the memory module 17, and is preferably rigidly mounted in order to support the memory module 17 within the interior compartment 25. The other side of the connector is connected to the microprocessor 22 via the data recorder interface 29. If the enclosure 18 is to be permanently secured to the monitor unit 20, then there may be no need for means for disconnecting the connector 19 from the data recorder interface 29. However, if disconnection is desired, the connector 19 and the data recorder interface 29 may utilize additional connectors, designed to mate together, to permit the patient data recorder 16 to be disconnected from the monitor unit 20 and removed. The selection of suitable connectors would be obvious to one of ordinary skill in the art. If used, these connectors may be rigidly affixed in place on the enclosure 18 and the monitor unit 20, respectively, to provide a more stable connection.

The memory module 17 includes a recording medium of a standard type generally referred to as non-volatile memory, in that the memory module 17 retains data while it is connected to the monitor unit 20 as well as when the memory module 17 is removed from the monitor unit 20. The memory module 17 must be able to perform both a "Read" function and a "Write" function. In addition, it is preferable for relatively small portions of the recording medium to be erased "on the fly," to enable new data to be stored in place of the oldest existing data on the medium, as described below. Erasure may be easily accomplished using well-known techniques. Preferred non-volatile recording medium types which may be suitable for use in the preferred embodiments of the present invention include "flash" memory and hard drives. Flash memory generally has the advantages of being quieter, faster, smaller, lighter, and less prone to mechanical failure because it has no moving parts. However, in applications where cost may be a factor, or where larger memories are required, a hard drive may be used instead. In addition, other memory devices, such as optical cards, optical disks, magneto-optical disks and IC RAM cards with or without separate batteries, could also perform these same functions.

The memory module 17 also includes its own I/O port and interface (not shown) for connecting the memory module 17 to the monitor unit 20 via the connector 19 of the patient data recorder 16. The I/O port and interface types are selected to correspond to the connector 19 of the patient data recorder 16 and the data recorder interface 29 of the monitor unit 20, respectively. An interface suitable for use in the preferred embodiments of the present invention is the well-known PCMCIA interface, which permits devices to be connected together in a "plug and play" relationship, thus minimizing setup and maximizing ease of use. However, other interfaces and protocols may likewise be used without departing from the scope of the present invention. Their selection, which may be dependent on the type of recording medium utilized, would be easily accomplished by one of ordinary skill in the art.

The size of the memory space in the memory module 17 is dependent upon the number of characteristics to be monitored, the type of data to be collected for each characteristic, the precision or resolution with which the data is to be recorded, the frequency with which the data is collected, and perhaps most significantly, the length of time for which data is to be preserved in the memory module 17 at any given moment. With regard to the number of characteristics and type of data to be collected, it should be noted that not all of the patient data monitored by the monitor unit 20 necessarily needs to be recorded in the patient data recorder 16. In one of the preferred embodiments, however, the four vital signs identified hereinabove as being particularly important are monitored and recorded: respiration, temperature, heart rate, and blood pressure. These vital signs are often regarded as being the most basic indicators of a patient's status, and are certainly among the most frequently-monitored vital signs.

The precision or resolution required for the data may vary depending on the type of data involved. By way of example, a respiration value in the range [0%-100%] would require 7 bits to provide accuracy to the nearest 1%; a temperature value in the range [−1° C. to 46° C.] would require 9 bits to provide accuracy to the nearest 0.1° C.; a heart rate value in the range [30/bpm to 300/bpm] would require 8 bits to provide accuracy to the nearest 1 bpm; and a blood pressure value in the range [10 mm to 275 mm] would require 6 bits to provide accuracy to the nearest 5 mm. Notably, because the precision of the data is limited by the resolution of the A/D converter(s) 126 utilized, the size of the A/D converter(s) 126 should be selected accordingly. Also, it may be useful to standardize, where possible, the resolution of each value at 8 bits (1 byte) in order to function smoothly with the memory module 17. This may be particularly true if the memory module 17 to be used is addressable in units of 8 bits. The selection of a suitable precision for the various data values would be easily accomplished by one of ordinary skill in the art.

The sampling frequency may be selected in conjunction with the selection of the data to be recorded and the resolution to be used. Certain vital signs, such as, by way of example, an ECG signal, may require relatively high sampling rates on the order of between 64 and 1024 samples each second, while other, more slowly-changing values, such as temperature or heart rate, may not need to be sampled more than once every second. Notably, it is not required that the number of samples recorded be the same as the number generated. In other words, samples may be generated that are not recorded on the memory module 17, or, if a new sample is not available when the microprocessor 22 is ready to write to the memory module 17, then the most recently-obtained value may be rewritten. The latter technique may, for example, help avoid the necessity for complicated processing methods for recording samples of some vital signs in the memory module 17 more often than others. On the other hand, recording duplicate samples would use more memory space than would otherwise be required.

An important factor in determining memory size is the need to keep vital sign data for a long enough period of time to ensure that it is still available should subsequent examination of the data be necessary. For example, an event such as the death of a hospital patient may warrant, as part of a standard procedure, the retrieval and examination of the memory module 17 from monitor/recorder system 10 that was used by the hospital while caring for the patient. However, such a death might occur hours or even days after the care was actually given. Thus, in order to ensure that the desired data is still available when needed, it may be useful to establish a minimum period of time for data recorded in the patient data recorder 16 to be preserved before being overwritten. As described previously, one approach is the frequent physical removal and warehousing of the memory modules 17 from the patient data recorders 16. However, it may be more efficient to instead use a memory module 17 having sufficient memory space to preserve all data corresponding to the minimum period of time in the memory space itself. The minimum period of time may be selected by the user on the basis of how the system 10 is to be used, but in typical applications the period of time may be in the range of 1 day to 1 month. However, applicability may be found for systems 10 that preserve data for only a matter of hours or for a matter of months.

In one exemplary embodiment, sampling four electrical signals, each representing one of the four parameters identified above, at a rate of 128 times each second, and recording an 8-bit value corresponding to each sample, would generate 44 MB of data in a 24-hour period. This could easily be accommodated in a memory module 17 having 64 MB of memory space. In another exemplary embodiment, sampling six signals 256 times each second and recording an 8-bit value corresponding to each sample would generate 928 MB of data in a 7-day period. This could easily be accommodated in a memory module 17 having 1 GB of memory space. In yet another exemplary embodiment, sampling two signals 128 times each second and four more signals once each second, and recording an 8-bit value corresponding to each sample at the same rate, would generate 673 MB of data in a 30-day period. This could likewise easily be accommodated in a memory module 17 having 1 GB of memory space.

If the module-removal technique is utilized, then it should be apparent that either the original memory module 17, or a different memory module 17 having similar characteristics as the original, may be used for the next recording. Data previously stored in a memory module 17 may be erased, prior to re-recording, either by external means or by the monitor unit 20 itself, using well-known techniques.

Each memory module 17 requires little post-manufacture preparation other than to format the medium in an industry standard format, such as a disc operating system (DOS) format or any other format, random or defined, that is suitable for this application, and to have one blank file placed on the memory module as a contiguous file to collect the patient data. Formatting is normally done by the supplier of the memory module 17 or through the use of a PC with a PCMCIA interface or other corresponding port and utility software. If the recording media has been used, it is preferable, though not required, for it to be erased before reinstalling the memory module 17 in the enclosure 18.

In an alternative preferred embodiment of the present invention, the monitor/recorder system 10 may also be used to acquire and record voice data along with, or even instead of, vital sign data. In addition to statements or other utterances made by the patient being monitored, other sounds could be recorded, including doctor or other caregiver or staff statements and utterances as well as non-oral noises made in the patient's room. These sounds may be very helpful for forensic or diagnostic purposes, particularly when recorded in conjunction with vital sign data, by giving an indication as to what was going on in the room when a particular set of symptoms, as described by the vital sign data, arose. In this embodiment of the present invention, the sensing devices 15 of the monitor unit 20 further include at least one microphone for capturing voice or other sound data and a speech analyzer for digitizing the sound data for recordation in the patient data recorder 16. Once in digital form, the sound data may be handled in the same manner as other patient data, as described herein. However, because suitable voice reproduction may require a sampling rate and sample size of, for example, 8000 Hz and 8 bits, respectively, the capacity of the memory module 17 may need to be adjusted accordingly to handle the larger volume of data that is generated. In operation, the monitor/recorder system 10 is powered up and the vital sign sensing devices 15 are connected or applied to a patient. At the same time, information identifying the patient may be entered into the monitor unit 20. Preferably, an interlock system is provided for automatically preventing the monitor unit 20 from operating to gather vital sign information unless the patient data recorder 16 is operable. In this way, it is impossible, or at least unlikely, for the monitor unit 20 to be operated without recording at least some of the gathered data on the memory module 17 of the patient data recorder 16. The interlock system includes a master circuit, which disables the collection of vital sign data from the sensing devices 15, and a trigger. The trigger for the interlock system may be as simple as automatically transmitting an electrical signal from the memory module 17 to the microprocessor 22 when the memory module 17 is properly installed in the patient data recorder 16 or may include a more complex software interface between the microprocessor 22 and the memory module 17 that automatically provides the microprocessor 22 with a continuous indication of the amount of remaining data space on the memory module 17, the last time data was deleted from the memory module 17, or the like. The design and implementation of trigger mechanisms of various types suitable for use with the present invention will be apparent to persons of skill in the art.

Preferably, the interlock system is utilized every time operation of the system 10 is initialized and may even be utilized continuously during operation of the system 10 to ensure that the memory module 17 continues to remain operational. However, it should be understood that other features of the present invention may be utilized even in the absence of such an automatic mechanism.

The interlock system may also include deactivation means, including an override circuit and a user interface, for manually overriding the master circuit. If such deactivation means is provided, then a user may enable operation of the monitor unit even when the patient data recorder 16 is inoperable. Such a device may be useful when the functionality of the monitor unit 20 is needed, but the patient data recorder 16 is out of service for any of a variety of reasons. In a simple embodiment, the user interface includes only a simple switch, and overriding the master circuit may be accomplished merely by pressing or toggling the switch. However, use of the deactivation means is preferably limited, either through the use of operational policies established by the facility in which the monitor/recorder system 10 is used, by automated means, or both. The user interface may include one or more devices to facilitate these measures. For example, a warning light or message may be displayed to remind the user that the patient data recorder 16 is inoperable, that operation of the monitor unit 20 without an operable patient data recorder 16 is against hospital policy, or the like, or the user may required to enter information identifying himself to the system 10, and may be required to enter a password matching the identifying information.

Once the system 10 is fully operational, the sensing devices 15 may begin collecting vital sign data from the patient. The vital sign data gathered from the patient is automatically relayed to the monitor unit 20, where it may be processed by the microprocessor 22 in concert with the graphics processors, if utilized, for display on the display units 150. At approximately the same time, as the microprocessor 22 receives the vital sign data, at least some of the data is forwarded to the patient data recorder 16 via the data recorder interface 29. As described previously, the number of samples of a particular signal that are forwarded from the monitor unit 20 to the patient data recorder 16 may be greater or less than the total number of sample values gathered.

Figure 4:
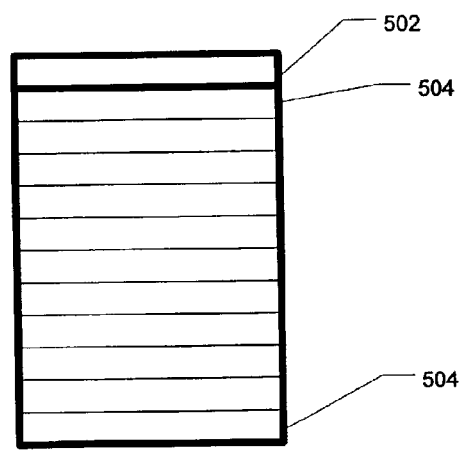
FIG. 4 is a diagram illustrating a data block format suitable for use in a preferred embodiment of the present invention.

In a method suitable for use with the preferred embodiments of the present invention, the sample values are organized into standardized blocks of data 500. FIG. 4 is a diagram illustrating a data block format suitable for use in a preferred embodiment of the present invention. Each block of data 500 preferably includes a control portion 502 and a data portion 504. The control portion, whose size depends on the control information included therein, preferably includes time/date data in the form of a time/datestamp and may include other data-independent information, such as a patient identifier, a memory module identifier, a monitor unit identifier, a patient data recorder identifier, a monitor/recorder system identifier, a room number, a user identifier, and the like, as well as data-dependent information, such as information identifying the number and type of vital sign signals included in the data block 500, the number of samples included in the data block 500, the amount of "real" time covered by the samples in the data block 500, and the like. The time/date data preferably includes a time/datestamp from the RTC 128 of the monitor unit, but may also include time/date data from other RTC's or from other clocks or oscillators not set to reflect an actual time of day. If multiple time/date data are provided, then the various data may subsequently be compared to each other to verify that time and day information has been actually recorded or to identify any instances of intentional or unintentional corruption of recorded data.

The control portion 502 may also include a predetermined code signaling the beginning of a data block 500, and may include a predetermined password. The data portion 504 includes at least one value, and preferably a plurality of values, representing vital sign data samples. The number of samples included in each data block 500 may be predetermined, and although a the data portion 504 may include only a single sample, it is preferable to include a larger number of samples in the data portion 504 of each data block 500. The number of samples is preferably selected to minimize the consumption of memory space by control information while ensuring that control information is recorded often enough to minimize the number of unidentified samples.

In addition to the standardized blocks of data 500, an individual block (not shown) of information may be recorded at the beginning of a recording session, at the end of a recording session, or both. These individual blocks may include general information such as the time the monitor/recorder system 10 was powered on or off, when the recording session started and ended, and the like. Some of the information stored in the control portion of the standardized data blocks 500 may instead be stored in these individual blocks or even in both locations, if desired.

As the patient data recorder 16 receives each successive data block 500, the data block 500 may be stored beginning at the next sequential memory location in the memory module 17. An address pointer to the address of the next sequential memory location may be stored in a predefined location in the memory space of the memory module 17, and may be incremented as memory locations are filled. When the available memory space of the memory module 17 is filled, the address pointer may be reset and the memory space may be reused, beginning at the first memory location and continuing sequentially from there. The existing data may either be erased in preparation for reuse or may be written over. In this way, the data stored in the memory module 17 at any given time is always the most recently-stored data, and a maximum amount of such data is always preserved.

The foregoing description generally assumes that the patient data recorder 16 is set up to receive vital sign data from a predetermined set of sensing devices 15 and that all of the expected data is actually collected by the monitor unit 20. However, there will frequently be situations where a user fails to utilize all of the sensing devices 15 in the predetermined set, either intentionally or by oversight, and thus not all of the anticipated data is actually collected. In such situations, the microprocessor 22 may be programmed to pad the corresponding locations in the standardized data blocks 500 that are to be stored in the memory module 17 with "zeroes" or another predetermined value. Alternatively, in order to save memory space, an additional set of identification bits, identifying those vital sign signals that are being monitored, may be stored at the beginning of each data block 500, as referred to hereinabove. Other methods for handling the problem will be apparent to those of ordinary skill in the art.

Preferably, tight security controls are included to prevent data stored in the memory module 17 from being destroyed or corrupted for as long as possible. Such controls may include preventing any data from being written to the memory module 17 other than that received from the monitor unit 20. However, even if the only means provided for erasing or overwriting data in the memory module 17 is the aforementioned method of recording new data in place of the oldest existing data in the memory module 17, it may be possible to accidentally or intentionally overwrite valuable data by operating the monitor unit 20 for an extended period of time without any sensing devices 15 in place, thus recording blank data over the existing valid data.

In order to prevent the effective erasure of valuable data merely by operating the monitor unit 20 without any sensing devices 15 attached or applied to a patient, the microprocessor 22 may optionally be programmed not to forward any data at all to the patient data recorder 16 until one or more of the sensing devices 15 in the predetermined set of sensing devices 15 are receiving valid data. In one approach, data will not be considered valid if it does not vary over a predetermined period of time, as valid data would. For example, if the value of a particular vital sign remains at zero for more than an hour, then it might be concluded that this data is invalid. In another approach, data could be rejected if its value falls outside an expected range, either instantaneously or for a predetermined period of time. Other approaches will be apparent to one of ordinary skill in the art. In addition to preventing invalid data from being intentionally recorded in the patient data recorder 16, some of these approaches could likewise be used to cause the automatic shutdown of the system 10 if it is clear that the system is not longer in use, thus saving power, wear and tear on the system 10, and battery life.

In many situations, however, it may be desirable to record all data generated or gathered by the monitor unit 20, regardless of whether it is valid or invalid. For example, in determining, after the fact, why a particular medical treatment was initiated at a particular point in time, it may be useful to have available all data that the caregiver may have had access to when the treatment was initiated, whether that data was, in fact, valid or invalid. Thus, it may not be desirable to use techniques such as those described above to identify invalid data. Alternatively, it may be preferred to prevent invalid data from being recorded only when every sensing device 15 is reporting invalid data simultaneously. In order to provide greater flexibility in circumstances such as these, it may be preferable to include password-protected software management tools for controlling whether invalid data is to be identified and deleted or not. An authorized user would then be able to control the use of techniques such as those described above. If one or more of these techniques are to be used, then the software management tools preferably also enable a user to adjust parameters related to the techniques. For example, if data is to be identified as invalid if it falls outside a particular numerical range, then the software management tools may permit the user to adjust the limits of that range.

Although the above-described approach of continuously replacing the oldest data in a particular memory module 17 with newly-gathered data is preferred because of its cost, another approach suitable for use with the present invention is to remove the memory module 17 from the patient data recorder 16 once it is substantially full of data and replace it with a fresh one. The newly-removed memory module 17 may then be stored in a secure location for as long as desired in order to preserve the data stored therein. Because of the cost inherent in storing every such module 17 indefinitely, it may be preferable to institute a standard procedure by which old modules are periodically erased and returned to use in a patient data recorder 16. If security of the memory modules 17 and their contents is critical, then only specially authorized personnel should be involved in carrying out any of these steps. Also, in a preferred embodiment suitable for use with this approach, a means is provided for tracking the amount of available memory space remaining and alerting a user when this space is nearly exhausted. This may be accomplished by storing and regularly updating a variable representing the total time the monitor unit 20 has been operated since the memory module 17 was last changed, or by calculating the remaining space on the fly on the basis of the address pointer and the total capacity of the memory module 17.

It is anticipated that in many or perhaps most cases, the data preserved using the above-described procedures is eventually discarded without ever being reviewed. However, under certain circumstances, referred to herein as "events," some level of review of a particular data set may be necessary. The determination of what types of circumstances may constitute an event may be made by a variety of individuals, including, but not limited to, medical practitioners, educators, clinicians or clinical investigators, administrators, independent agencies, and state and federal boards and investigators. The rules and procedures that are established for each type of event may vary with the type of data that is required. For example, educators may need to evaluate trends or prove an appropriate protocol. A peer review board may need to substantiate a backdrop for sentinel events. Administrators may need to better document a method of protocol change. Independent agencies may need to ensure documentation of events and develop the rules for sentinel events. State boards may need to establish a backdrop of hard data over which they can overlay event rebuilding or recounting. State and federal investigators may need hard data for evidence as dictated by law or by state boards. Each type of situation may require or merit a different volume of data, a different procedure, a different preservation period, or the like.

Regardless of how it is defined, when a predetermined triggering event occurs, the memory module 17 may be removed from the patient data recorder 16 and the data stored therein examined. This may be accomplished by first unlocking or unfastening any security devices and opening the access portal 21 to expose the memory module 17. It may also be desirable to power down the patient data recorder 16 in order to prevent damage to the memory module 17. The memory module 17 may then be removed using a method appropriate to the type of memory device used. If the monitor/recorder system 10 is to be returned to service immediately, then a replacement memory module 17 may be installed and the access portal 21 closed and secured once again. Preferably, the memory module 17 may then be transported to a secure location for analysis of the data therein. However, it should be clear that if desired, a user may instead download the data contained in the memory module 17 at the site of the monitor/recorder system 10 for analysis, then or in the future, thus permitting the memory module 17 to be returned to service immediately. Of course, in the latter method, the memory space on the memory module 17 is likely to be rewritten soon thereafter, thus preventing future analysis of the memory module 17 itself.

Once removed, the memory module 17 may be connected to a suitable peripheral device, such as a personal computer, so that the data may be examined. A docking station may be utilized to make connection to the peripheral device more convenient. Adaptability may be enhanced if the memory module 17 utilizes a standard I/O port and interface. However, if desired, an additional layer of security may be provided by utilizing a proprietary port or interface, or both. Once communication has been established between the memory module 17 and the peripheral device, a software application may be used to analyze each data block 500, extracting control information from the control portion 502 and organizing the individual data samples in the data portion 504 into their respective vital sign signals. Assuming that each data block 500 includes more than one sample of a particular vital sign signal, then it may be desirable to derive a precise time/datestamp for each sample from the time/datestamp information (and time period data, if provided) in the control portion 502. If desired, the software application may also be designed to permit other control information provided in the control portion 502 of each data block 500 to be matched to individual data samples. The software application may also include a GUI for enabling a user to control the operation of the software application. The GUI may also enable the user to display the extracted vital sign signals on a display unit and may include other software tools, or interfaces to such tools, to permit the data itself to be analyzed. Preferably, however, the integrity of the original memory module 17 itself is preserved at all times, and care should be taken to prevent the data contained therein from being destroyed or otherwise corrupted.

As noted previously, in an alternative embodiment, the entire patient data recorder 16 may be separated from the monitor unit 20. In this embodiment, when a need arises to investigate a particular medical phenomenon, the entire patient data recorder 16, rather than the memory module 17, may be removed from the system 10 so that the data stored on the memory module 17 therein may be accessed. In this embodiment, a suitable means for accessing the data on the memory module 17 via the connector 19 must be provided. However, the same general principles described in the preceding paragraphs pertaining to the removal and handling of the memory module 17 likewise apply to the removal and handling of the patient data recorder 16 as a whole, as would be apparent to one of ordinary skill in the art. This may have the advantage of physically protected the memory module 17, which may be rather delicate, from damage during handling.

Figure 5:
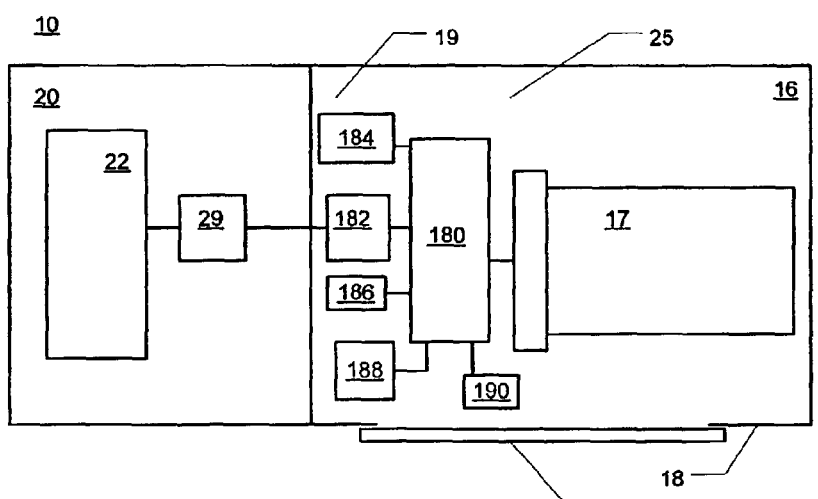
FIG. 5 is a schematic diagram of the monitor/recorder system of FIG. 1A illustrating the components of the patient data recorder in accordance with an alternative preferred embodiment of the present invention.

The integrity of the memory module 17 may be further protected in a variety of ways. FIG. 5 is a schematic diagram of the monitor/recorder system 10 of Fig. 1A illustrating the components of the patient data recorder 16 in accordance with an alternative preferred embodiment of the present invention. As illustrated therein, the patient data recorder 16 may further include its own microprocessor 180, an interface 182 for communicating with the monitor unit's data recorder interface 29, and an interface for communicating with the connector 19 to the memory module 17. In addition, the patient data recorder 16 may also include a variety of peripheral components, all of which may be mounted on a single printed circuit board. The peripheral components may include a separate power subsystem 184, an RTC 186, a user interface subsystem 188 and an oscillator 190. The patient data recorder's power subsystem 184 and oscillator 190 may be similar to those of the monitor unit 20, but are preferably physically inaccessible to ordinary users without a key, special tool, password or the like. This may help to prevent malevolent users from being able to tamper with the patient data recorder 16 by removing or damaging its battery or other portions of its power subsystem 184 or its oscillator 190. Similarly, a separate RTC 186 may be used to keep track of real-time time and day information and to provide this information to the data recorder microprocessor 180. Like the RTC 128 of the monitor unit 20, it may have its own crystal oscillator and power backup circuitry. By making the data recorder RTC 186 physically inaccessible, the integrity of the time/datestamp information for the patient data recorder 16 may be further protected.

Although not necessary, a user interface subsystem 188 may be utilized to make access and operational control of the patient data recorder 16 more straightforward. The user interface subsystem 188 may include a display (not shown) and a keypad (not shown). The display has sufficient space to display simple messages to a user in text format. In a preferred embodiment, the display is an LCD-type display that includes at least two lines of twenty text characters each (2×20) and that may or may not include a backlight. The LCD preferably communicates with the data recorder microprocessor 180 via an interface that includes a 4-bit data bus and a factory-preset contrast adjustment resistor. The keypad may be a standard membrane keypad wired in a simple X-Y matrix. The keypad may include a set of numeric keys plus other special function keys for inputting data into the microprocessor 180.

In other alternative preferred embodiments, additional software mechanisms may be used to protect further data security. For example, access to the software application itself may be password protected, but the software application may also be prevented from using the control information to properly access the data if the user is unable to provide the password that is stored in the control portion 502 of each data block 500. Multiple levels of control may be established, with classes of users defined for each level of control. For example, one class of users may be authorized to view data, while another class of users may be authorized to modify or delete data. Still further, an encryption method may be used to provide further data security. A wide variety of encryption methods are well known in the art. Unfortunately, drawbacks to using encryption may include slower operation, which in turn may affect the ability of the patient data recorder 16 to record the desired number of samples, and the consumption of additional memory space in the memory module 17. However, because the same user may be in control of both the patient data recorder 16 and the personal computer or other device used to recover the data from the memory module 17, there is no need to distribute encryption or decryption "keys" to third parties. Thus, both of these problems may be minimized through use of simpler encryption methods than would be necessary to achieve secure communication between two separate parties.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A method of encouraging the recordation of patient vital sign data, comprising the steps of:
   (a) providing a monitor and recorder system, the monitor and recorder system including at least one sensing device, a microprocessor, a memory module, and a user interface subsystem;
   (b) during operation of the monitor and recorder system, automatically determining, via an interlock system and the microprocessor, whether the memory module is prepared to accept vital sign data received by monitor and recorder system;
   (c) if, in the determining step, it is determined that the memory module is prepared to accept vital sign data:
      (i) receiving vital sign data information from a patient via the at least one sensing device of the monitor and recorder system,
      (ii) displaying the vital sign data, and
      (iii) recording the vital sign data on the memory module,
      (iv) wherein the receiving, displaying, and recording steps are carried out at least partly under control of the microprocessor; and
   (d) if, in the determining step, it is determined that the memory module is not prepared to accept vital sign data, carrying out the steps, at least partly via the microprocessor, of:
      (i) via the user interface subsystem, warning an operator of the monitor and recorder system that the memory module is not prepared to accept vital sign data, and
      (ii) concurrently therewith, controlling the monitor and recorder system to automatically prevent the vital sign data from being displayed,
      (iii) wherein the warning and controlling steps are carried out at least partly under control of the microprocessor.

2. The method of claim 1, wherein the monitor and recorder system is a bedside monitor and recorder device, and wherein the method further comprises the step of positioning the monitor and recorder system adjacent the patient.

3. The method of claim 1, wherein the user interface subsystem includes a display unit, and wherein the data displayed in the displaying step is displayed in a graphical format.

4. The method of claim 1, wherein the user interface subsystem includes a display unit, and wherein the data displayed in the displaying step is displayed in a numerical format.

5. The method of claim 1, wherein the user interface subsystem includes a display unit, and wherein the data displayed in the displaying step is displayed in a textual format.

6. The method of claim 1, wherein the step of providing the monitor and recorder system includes providing a user interface subsystem that incorporates a display unit.

7. The method of claim 1, wherein the step of providing the monitor and recorder system includes providing a display unit that includes a plurality of distinct display units.

8. The method of claim 1, wherein the step of providing the monitor and recorder system includes providing a display unit that is a single display unit that includes a plurality of display areas therein.

9. The method of claim 1, further comprising a step, if in the determining step it is determined that the memory module is prepared to accept vital sign data, of externally communicating data, representative of the vital sign data gathered from the patient, to a remote device via a communication interface of the monitor and recorder system.

10. The method of claim 9, wherein the step of externally communicating data to a remote device includes externally communicating data to a remote device that is not physically present in a room in which the patient is located.

11. The method of claim 9, wherein the step of displaying data includes displaying data on the remote device.

12. The method of claim 11, wherein the step of displaying data includes displaying data on the remote device and also includes displaying data on a display unit disposed adjacent to the monitor and recorder system.

13. The method of claim 9, further comprising a step of connecting the remote device to the monitor and recorder system via a communications network.

14. The method of claim 9, wherein the remote device is a personal computer, the method further comprising connecting the personal computer directly to the monitor and recorder system.

15. The method of claim 9, wherein the step of providing the monitor and recorder system includes incorporating the memory module in the remote device.

16. The method of claim 15, further comprising a step of communicatively connecting the remote device is to the monitor and recorder system via wired connection.

17. The method of claim 15, further comprising a step of communicatively connecting the remote device is to the monitor and recorder system via wireless connection.

18. The method of claim 1, wherein the providing step includes enclosing the memory module and the monitor and recorder system within the same integral enclosure.

19. The method of claim 1, wherein the microprocessor is enclosed in a first structure, and wherein the providing step includes enclosing the memory module in a second structure that is separate from the first structure.

20. The method of claim 19, wherein the providing step includes enclosing the memory module in a second structure that is separate from the first structure but securely fastened to the exterior thereof.

21. The method of claim 19, wherein the providing step includes electrically connecting the memory module and the other elements of the monitor and recorder system.

22. The method of claim 21, further comprising steps, if in the determining step it is determined that the memory module is prepared to accept vital sign information received by the monitor and recorder system, of:
   externally communicating data, representative of the vital sign data gathered from the patient, to a remote device via a communication interface; and
   displaying data on the remote device.

23. A method of encouraging the recordation of patient vital sign data, comprising the steps of:
(a) providing a monitor and recorder system, the monitor and recorder system including at least one sensing device, a microprocessor, a memory module, and a user interface subsystem;
(b) during operation of the monitor and recorder system, automatically determining, via an interlock system and the microprocessor, whether the memory module is prepared to accept vital sign data received by monitor and recorder system;
(c) if, in the determining step, it is determined that the memory module is prepared to accept vital sign data:
  (i) receiving vital sign data information from a patient via the at least one sensing device of the monitor and recorder system, and
  (ii) recording the vital sign data on the memory module,
  (iii) wherein the receiving and recording steps are carried out at least partly under control of the microprocessor; and
(d) if, in the determining step, it is determined that the memory module is not prepared to accept vital sign data:
  (i) controlling operation of the monitor and recorder system at least by providing a user-perceptible indication, via the user interface subsystem, to warn an operator of the monitor and recorder system that the memory module is not prepared to accept vital sign data, and
  (ii) concurrently therewith, controlling the monitor and recorder system to automatically prevent the vital sign data from being received thereby,
  (iii) wherein controlling steps receiving, displaying, and recording steps are carried out at least partly under control of the microprocessor.

* * * * *